United States Patent
Woods et al.

(10) Patent No.: US 6,673,192 B1
(45) Date of Patent: Jan. 6, 2004

(54) MULTI-AMINE COMPOUND PRIMERS FOR BONDING OF POLYOLEFINS WITH CYANOACRYLATE ADHESIVES

(75) Inventors: John G. Woods, Farmington, CT (US); Jean M. J. Fréchet, Oakland, CA (US)

(73) Assignee: Loctite Corporation, Hartford, CT (US)

(*) Notice: Subject to any disclaimer, the term of this patent is extended or adjusted under 35 U.S.C. 154(b) by 0 days.

(21) Appl. No.: 08/937,722

(22) Filed: Sep. 25, 1997

(51) Int. Cl.$^7$ ............................................. B32B 31/00
(52) U.S. Cl. .................. 156/314; 156/331.2; 106/287.3; 427/412.3; 564/512
(58) Field of Search .................. 156/314, 331.2; 106/287.3; 564/512; 427/412.3

(56) References Cited

U.S. PATENT DOCUMENTS

| | | |
|---|---|---|
| 2,330,033 A | 9/1943 | D'Alelio |
| 2,748,050 A | 5/1956 | Shearer et al. |
| 3,197,318 A | 7/1965 | Halpern et al. |
| 3,260,637 A | 7/1966 | Bramer et al. |
| 3,523,097 A | 8/1970 | Coover et al. |
| 4,143,003 A | 3/1979 | Haas et al. |
| 4,313,865 A | 2/1982 | Teramoto et al. |
| 4,477,607 A | 10/1984 | Litke |
| 4,507,466 A | 3/1985 | Tomalia et al. |
| 4,533,422 A | 8/1985 | Litke |
| 4,556,700 A | 12/1985 | Harris et al. |
| 4,631,337 A * | 12/1986 | Tomalia et al. .............. 564/512 |
| 4,695,615 A | 9/1987 | Leonard et al. |
| RE32,889 E | 3/1989 | Litke |
| 4,814,427 A | 3/1989 | Fukuda et al. |
| 4,822,426 A | 4/1989 | Ito et al. |
| 4,869,772 A | 9/1989 | McDonnell et al. |
| 4,906,317 A | 3/1990 | Liu |
| 4,979,993 A | 12/1990 | Okamoto et al. |
| 5,079,098 A | 1/1992 | Liu |
| 5,110,392 A | 5/1992 | Ito et al. |
| 5,133,823 A | 7/1992 | Nicolaisen et al. |
| 5,135,598 A | 8/1992 | Kobe et al. |
| 5,288,794 A | 2/1994 | Attarwala |
| 5,292,364 A | 3/1994 | Hiraiwa et al. |
| 5,306,752 A | 4/1994 | Attarwala |
| 5,314,562 A * | 5/1994 | McDonnell et al. ......... 156/314 |
| 5,328,944 A | 7/1994 | Attarwala et al. |
| 5,359,101 A | 10/1994 | Woods et al. |
| 5,386,047 A | 1/1995 | Nakos et al. |
| 5,424,343 A | 6/1995 | Attarwala |
| 5,527,524 A | 6/1996 | Tomalia et al. |
| 5,567,266 A | 10/1996 | Liu |
| 5,610,268 A | 3/1997 | Meijer et al. |

FOREIGN PATENT DOCUMENTS

| | | |
|---|---|---|
| EP | 0271675 | 6/1988 |
| EP | 0 476 203 A1 | 3/1990 |
| EP | 0476203 | 3/1992 |
| EP | 0 691 328 | 1/1996 |
| GB | 1168000 | 10/1969 |
| JP | 55-94979 * | 7/1980 .............. 156/331.2 |
| JP | 61-136567 | 6/1986 |
| WO | 92/09669 | 6/1992 |

OTHER PUBLICATIONS

E. Buhleier et al, "Cascade–and Nonskid–Chain–likeSynthesis of Molecular Cavity Topologies," *Synthesis*, 1978, pp. 155–158.

Coleshill, A., et al, *Polymer Preprints*, 38, (1) 135 (Apr. 1997).

Yang J., et al, "Primers for Adhesice Bonding to Polyolefins," *J. Applied Polymer Sci.*, 48, 359–370 (1993).

McDonnell, P., "Bonding of Polyolefins with Cyanoacrylate Adhesices," *Adhesion* (London) 15, 69–79, (1991).

Okamoto, Y., et al., "Primers for Bonding Polyolefin Substrates with Alkyl Cyanacrylate Adhesive," *J. Adhesion*, 81–91 (1993).

Yang, D., *Surface and Interface Analysis*, 20, 407 (1993).

Yang, D., "Analysis of the Polyolefin/Trialkylamine Primer Interface," *Surface and Interface Analysis*, 40, 81–91 (1993).

Okamoto, Y. and Klemarczyk, P.T., "Bonding Non–Polar Plastic with Alkyl Cyanoacrylate Instant Adhesive", *49th Annual Tech. Conf. –Soc. Plastic Eng.* (ANTEC '91), 1114–17, 1991.

F. Zeng et al, "Dedrimers in Supramolecular chemistsry: From Molecular Recognition to Self–Assembly", *Chem. Rev.*, pp. 1681–1682, 1997.

E. Malmstrom, et al, "Hyperbranched Aliphatic Polyesters", *Macromolecules*, pp. 1968, 1995.

S. Richard Truner et al, "All–Aromatic Hyperbranched Polyesters with Phenol an Acetate End Groups: Synthesis and Characterization", *Macromolecules*, pp. 4617, 1993.

Young H. Kim, et al, "Macromolecules", vol. 25, No. 21, pp. Oct. 12, 1992.

P. Flory, et al, "Principles of Polymer Chemistry", Cornell University Press, pp. 256–260, 1953.

G. Scherr et al, "Encyclopedia fo Chemical Technology", vol. 14, Kirk–Othmer 4th ed. pp. 22–23.

CA Abstract, AN 126:278506, "Primers for alpha cyanoacrylate adhesives in olefin polymer bonding", 1995.

Caplus Abstract AN 1988:456741, 1986.

CAPLUS Abstract AN 1996:54197, 1995.

(List continued on next page.)

*Primary Examiner*—Jeff H. Aftergut
(74) *Attorney, Agent, or Firm*—Robert O. Vidas

(57) ABSTRACT

Primers for cyanoacrylate adhesives which are based on compounds having multiple amine groups thereon ("multi-amines") which have at least three secondary or tertiary amine groups, at least one of which is a tertiary amine group. The multi-amine compounds are characterized by having thereon at least three terminal and/or pendant aliphatic hydrocarbon groups of at least 4 carbon atoms in length. Such primers give substantially improved bond strengths to cyanoacrylate adhesive bonded assemblies comprising a polyolefin substrate such as high density polyethylene, LDPE or polypropylene. The multi-amine may have a cascade, dendrimer, hyperbranched or comb-like structure.

36 Claims, No Drawings

OTHER PUBLICATIONS

CAPLUS Abstract AN 1994:559135, 1992.
CAPLUS Abstract AN 1993:82342, 1992.
CAPLUS Abstract AN 1994:166953, 1992.
CAPLUS Abstract AN 1993:429149, 1993.
CAPLUS Abstract AN 1992:614107, 1992.
CAPLUS Abstract AN 1992:237016, 1991.
CAPLUS Abstract AN 1991:45107, 1990.
CAPLUS Abstract AN 1990:516425, 1990.
CAPLUS Abstract AN 1990:499575, 1990.
CAPLUS Abstract AN 1990:480672, 1990.
CAPLUS Abstract AN 1989:194272, 1988.
CAPLUS Abstract AN 1988:456274, 1988.
CAPLUS Abstract AN 1987:215093, 1986.
CAPLUS Abstract AN 1987:197638, 1987.
CAPLUS Abstract AN 1987:197637, 1987.
CAPLUS Abstract AN 1987:6113, 1986.
F.B. Zienty, "Cyclic Thioureas", Journal of the American Chemical Society, vol. LXVIII, No. 7, Jul. 19, 1946, p. 1388 XP002091441.

* cited by examiner

MULTI-AMINE COMPOUND PRIMERS FOR BONDING OF POLYOLEFINS WITH CYANOACRYLATE ADHESIVES

FIELD OF THE INVENTION

The present invention pertains to cyanoacrylate adhesives which are cured using an activator compound having multiple amine functional groups thereon (a "multi-amine"), to the cured products thereof and to novel multi-amine activator compounds. The invention also pertains to a method of bonding substrates, especially nonpolar substrates such as polyolefins, using cyanoacrylate adhesives activated with certain multi-amine compounds, to bonded assemblies produced thereby.

BACKGROUND OF THE INVENTION

Compounds with a variety of highly branched architectures, such as "cascade," "dendrimer," "hyper-branched" and "comb-like," architectures, are known. As used herein, the terms "multi-amine cascade compounds," "multi-amine dendrimers," "multi-amine hyperbranched compounds" and "multi-amine comb-like compounds" refer to compounds having such branched architectures in which branching occurs via tertiary amine groups.

Cascade molecules are high molecular weight macromolecules with a very unique continuously branching structure emanating from a core unit. Formulae are characterized as having a geometrically increasing number of monomer derived branch units in each "generation" (the core being assigned generation 0, i.e. G0, and successive generations numbered sequentially, i.e. G1, G2, G3, etc). Idealized, such compounds are substantially monodisperse with all of the terminal groups being equidistant (measured through the chained bonds) from the core. However, frequently a given synthetic route will produce a distribution of macromolecules having branches of different lengths.

E. Buhleier, W. Wehner and F. Vögtle, "'Cascade'-and 'Nonskid-Chain-like' Synthesis of Molecular Cavity Topologies," *Synthesis*, 1978, pp 155–158, (incorporated herein by reference) reports that cascade poly (alkyleneamine) compounds may be obtained from Michael addition of acrylonitrile to a monoamine or diamine core molecule such as phenylmethyl amine and ethylenediamine, 1, 3,-di-(methylamino)benzene or 1,6-di(methylamino) pyridine, respectively, followed by reduction of the terminal nitrile groups to primary amine groups. Successive generations of such compounds, each increasing the number of branches on the molecule, are produced by repeating the Michael addition and nitrile reduction reactions on the previous generation product.

Multi-amine dendrimers, which may be considered to be substantially monodisperse cascade compounds, often with a generally spheroidal morphology may be prepared in a number of ways. In U.S. Pat. No. 5,610,268, incorporated herein by reference, poly(alkyleneamine) dendrimers are obtained by Michael additions of acrylonitrile or similar compounds to an active hydrogen functional core molecule such as 1,4-butanediamine, in like manner to the process of the E. Buhleier, W. Wehner and F. Vögtle paper discussed above. Generation numbers of three or more are described in this patent.

Poly(alkylester) dendrimers branching out from tertiary amino groups are described in Coleshill, A., et al, *Polymer Preprints*, 38(1) 135 (4/1997), (also incorporated herein by reference.) In this reference the branch units are derived from 2-(di-(t-butyldimethylsilyloxyethyl))aminoacetic acid monomer. The core is a polyol such as 1,4-dihydroxybenzene or 1,4-butanediol. The first generation dendrimer is prepared by esterification reaction between the core hydroxy groups and monomer acid group, followed by removal of protecting t-butyldimethylsilyl groups to give the multi-amine dendrimer having terminal hydroxyl groups. Successive esterification reactions of the dendrimer with monomer acid followed by deprotection of the t-butyldimethylsilyl groups of the monomer give successive generations of this multi-amine dendrimer.

Poly(alkylamide) dendrimers branching out from tertiary amino groups are described in U.S. Pat. No. 4,507,466, also incorporated herein by reference. In this patent Michael addition of methyl acrylate to ammonia or a primary amine core, followed by displacement of the ester with a diamine, such as ethylene diamine, produces a first generation dendrimer with primary amine terminated amide functional branch units. Successive Michael additions with methyl acrylate and diamine displacement reactions give successive generations of this multi-amine dendrimer.

Hyperbranched compounds are polymeric materials, typically prepared in a single polymerization step, with a very high degree of branching resulting from the choice of monomer and/or polymerization mechanism employed. The monomer may be an $AB_n$ type monomer, where A and B represent different reactive groups capable of undergoing an addition or condensation reaction with each other and n represents an integer equal to or greater than 2. Idealized fully branched homopolymer structures are similar to dendrimers but in practice the polymer molecules prepared in this way are characterized by a higher polydispersity and a lower degree of branching than an analogous dendrimer. Hyperbranched architectures may also result from chain transfer processes in conventional addition or ring opening reactions. Poly(ethyleneimine), prepared by ring opening polymerization of aziridines, is an example of this type of molecule and is a multi-amine compound.

Multi-amine molecules having "comb-like" architecture are characterized by a linear amine group-containing backbone with pendant side groups extending therefrom.

It has long been appreciated that cyanoacrylate adhesives give poor bonds when one or both substrates being bonded are nonpolar materials. This problem is particularly acute for polyolefin substrates and especially for low density polyethylene (LDPE). To improve bonding to such materials, a variety of primer activators have been employed with cyanoacrylate adhesives. Typically the activator is applied to one or both substrates neat or as a solution in a volatile solvent. The solvent, if present is dried and then the adhesive applied and the substrates promptly joined.

Organometallic compound primers for cyanoacrylate adhesives are described in JP 61-136567; U.S. Pat. No. 4,822,426; U.S. Pat. No. 5,110,392; U.S. Pat. No. 5,292,364 and Yang, J, et al., Primers for Adhesive Bonding to Polyolefins," *J Applied Polymer Sci.*, 48, 359–370 (1993).

Amine, amine salt or other nitrogen compound primers for cyanoacrylate adhesives are described in U.S. Pat. No. 3,260,637 (various secondary and tertiary mono and diamine compounds); U.S. Pat. No. 4,814,427 (mixture of aldehyde and organic amine); U.S. Pat. No. 4,869,772 (diazabicyclo and triazabicyclo compounds); U.S. Pat. No. 4,979,993 (tertiary ammonium alkylcarboxylates); U.S. Pat. No. 5,079,098 (quaternary ammonium compounds); U.S. Pat. No. 5,133,823 (imidazole derivatives); U.S. Pat. No. 5,135,598

(ethylenically unsaturated amine polymerized before the adhesive is applied); U.S. Pat. No. 5,314,562 (ethylenediamine and certain derivatives thereof); U.S. Pat. No. 5,567,266 (organic amines in certain carriers); EP 0476203 B1 (certain tertiary propylene and butylene diamines); EP 0271675 (mixture of aldehyde and organic amine); McDonnell, P., "Bonding of Polyolefins with Cyanoacrylate Adhesives," *Adhesion* (London), 15, 69–79, (1991); Okamoto, Y., et al., "Bonding Non-Polar Plastics with Alkyl Cyanoacrylate Instant Adhesive," *ANTEC'91* (49th Annu. Tech Conf.-Soc. Plast. Eng.), 1114–1117 (1991); Okamoto, Y., et al., "Primers for Bonding Polyolefin Substrates with Alkyl Cyanoacrylate Adhesive," *J. Adhesion*, 40, 81–91 (1993); and Yang, D., "Analysis of the Polyolefin/Trialkylamine Primer Interface," *Surface and Interface Analysis*, 20 407–415 (1993).

Heretofore 1,8-diazabicyclo[5,4,0]undec-7-ene (DBU) and tri-n-dodecylamine (TDA) have been found to be among the most useful polyolefin primer materials. These primers, however, give only a limited improvement in bond strength on the lowest energy surface materials, such as LDPE, and typically do not give bonds which fail by a substrate failure mode on LDPE. There is therefore a continued need for primer materials for cyanoacrylate adhesives which will give improved bonding to polyolefins, and in particular to LDPE.

SUMMARY OF THE INVENTION

The invention is directed to primer compositions for cyanoacrylate or related anionically polymerizable monomers. The primers employ a multi-amine compound in a volatile organic solvent. The multi-amine compound has at least three secondary or tertiary amine groups, at least one of which is-a tertiary amine group. The multi-amine compound also has at least three terminal and/or pendant aliphatic hydrocarbon groups of at least 4 carbon atoms in length thereon. The aliphatic hydrocarbon groups are suitably alkyl or alkenyl groups.

The primers of the invention give substantially improved bond strengths to cyanoacrylate adhesive bonded assemblies comprising a polyolefin substrate, such as a high density polyethylene, LDPE or polypropylene substrate. They give especially striking improvement when at least one of the substrates being bonded is LDPE.

The invention is also directed to cyanoacrylate adhesive compositions which include such multi-amine compounds, and to cured cyanoacrylate polymers and bonded assemblies produced by bringing an α-cyanoacrylate monomer into contact with such a multi-amine compound.

The invention is also directed to (certain novel multi-amine compounds) which are characteristically terminated with $C_4$ or higher alkyl or alkenyl groups. Such multi-amine compounds include the following:

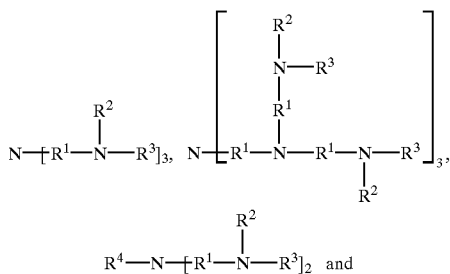

-continued

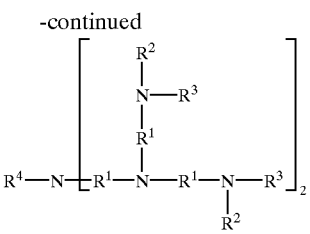

where R' is —$CH_2CH_2$— or —$CH_2CH_2CH_2$—; $R^2$ is H or $R^3$; the $R^3$ groups are the same different $C_4$–$C_{22}$ alkyl, alkenyl, carboxyalkyl, carboxyalkenyl or —$CH_2CH_2C(=O)OR^4$; and $R^4$ is $C_4$–$C_{22}$ alkyl. Linear or branched poly (alkylenimine) having at least three terminal and/or pendent groups defined as for $R^3$ are further multi-amine compounds of the invention.

DETAILED DESCRIPTION OF THE PREFERRED EMBODIMENTS

The anionically polymerizable monomers used to form the adhesive compositions of the invention have the generic formula:

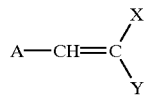

where X and Y are groups which are more strongly electron withdrawing than halo and A is H or $CH_2$=CH—. X and Y may be, for instance, —CN, —$COR^5$, —$COOR^5$, —$SO_2R^5$, $SO_3R^5$ where $R^5$ is H or an optionally substituted hydrocarbon group. (Specific examples of such monomer compounds include cyanoacrylate esters; 2-cyanopenta-2,4-dienoate esters; vinylidene cyanide; dialkyl methylene malonates as described in U.S. Pat. No. 2,330,033; U.S. Pat. No. 3,197,318 and U.S. Pat. No. 3,523,097; acylacrylonitriles, as described in GB 1,168,000 and vinyl sulfinates and sulfonates, as described in U.S. Pat. No. 2,748,050.)(Commercially, cyanoacrylate ester formulations are the most significant and for that reason are preferred.) The invention will therefore be described in connection with cyanoacrylate formulations. However the skilled person will recognize that this disclosure is also generally applicable to other monomers in the formula above and to mixtures thereof.

The α-cyanoacrylate adhesive compositions of this invention include one or more α-cyanoacrylate monomers of the formula:

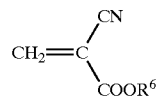

where $R^6$ represents $C_{1-16}$ alkyl, cycloalkyl, alkenyl, alkynyl, cycloalkenyl, alkaryl, aralkyl or aryl any of which may be optionally substituted by, or interrupted with, non-basic groups, such as oxo, silicon, titanium, halo and ether oxygen, which do not interfere with the stability and functioning of the monomer as an adhesive. Examples of $R^6$ include methyl, ethyl, n-propyl, isopropyl, n-butyl, isobutyl, pentyl, hexyl, allyl, methallyl, crotyl, propargyl, cyclohexyl, benzyl, phenyl, cresyl, 2-chlorobutyl, trifluoroethyl, 2-methoxyethyl, 3-methoxybutyl, and 2-ethoxyethyl. Cyanoacrylate esters containing silicon or titanium atoms are disclosed in U.S. Pat. No. 5,359,101, incorporated herein by reference, and such monomers may also be used.

A single α-cyanoacrylate monomer, or mixtures thereof may be used. Mixtures of α-cyanoacrylate monomers with other anionically polymerizable monomers may also be used, such as mixtures with di-α-cyanopentadienoate esters, as disclosed in U.S. Pat. No. 5,386,047, incorporated herein by reference.

(One or more of the following components are sometimes added to the α-cyanoacrylate monomer component of the adhesive: anionic polymerization inhibitors; radical polymerization inhibitors; thickeners; cure accelerators; plasticizers; tougheners; heat stabilizers for the cured polymer; perfumes; dyes; and, pigments.)

A suitable amount of the α-cyanoacrylate monomer present in the adhesive composition is about 75 to 99 by weight, based on the total weight of the adhesive composition.

An anionic polymerization inhibitor is usually added to the α-cyanoacrylate adhesive composition, typically in an amount of about 1 to 1000 ppm based on the total weight of the adhesive composition, to increase the stability of the adhesive composition during storage, and examples of known inhibitors are sulfur dioxide, $BF_3$, sulfur trioxide, nitric oxide, hydrogen fluoride, and certain sultones. Combinations of methane sulfonic acid (MSA) or hydroxypropane sulfonic acid (HPSA) with sulfur dioxide are suitable. Suitable concentrations of sulfonic acids range from about 5 to about 100 parts per million (ppm), more suitably about 10 to 50 ppm, based on monomer weight. Suitable concentrations of $SO_2$ range from about 2 to about 20 ppm.

The cyanoacrylate adhesive compositions of this invention may also contain an inhibitor of the free radical polymerization. Desirable free radical inhibitors include phenolic type inhibitors, such as quinone, hydroquinone, t-butyl catechol, p-methoxy-phenol, etc.

The above inhibitors may be used within wide ranges, but the following general guidelines are representative of the adhesive composition: acid gases, from about 1 ppm to about 600 ppm by weight; sultones, from about 0. 1% to about 2% by weight; sulfonic acids, from about 5 ppm to about 1000 ppm by weight; and free radical inhibitors, from about 0.001% to about 1%.

A thickener frequently is added to increase the viscosity of the α-cyanoacrylate adhesive composition. Various polymers can be used as thickeners and examples include poly(methyl) methacrylate, methacrylate-type copolymers, acrylic rubbers, cellulose derivatives, polyvinyl acetate, poly(α-cyanoacrylate) and mixtures thereof. A suitable amount of thickener is generally about 20% by weight or less based on the total weight of the adhesive composition.

A number of conventional polymer additives may also be added for toughening purposes. Examples include ethylene-acrylic elastomers and other acrylic elastomers, acrylonitrile copolymer elastomers, and fluoro elastomers. In appropriate amounts such materials may serve as both thickener and toughener. Suitable toughening polymers, and cyanoacrylate formulations incorporating such polymers, are described in U.S. Pat. No. 4,440,910, incorporated herein by reference.

Certain fumed silica fillers may also be usefully employed as cyanoacrylate thickeners. A number of such silicas are known. Silicas treated with polydialkylsiloxanes or trialkylsilanes are suitably employed as disclosed in U.S. Pat. No. 4,477,607, U.S. Re. Pat. No. 32,889 and U.S. Pat. No. 4,533,422, all of which are incorporated herein by reference.

As examples of cure accelerators there are known, for instance, crown ethers, crown ether analogs, and other compounds such as are disclosed in U.S. Pat. No. 4,313,865 at column 4, line 36—column 5, line 52; calixarene compounds as described in U.S. Pat. No. 4,556,700 and U.S. Pat. No. 4,695,615; and silacrown compounds as described in U.S. Pat. No. 4,906,317, all of which are incorporated herein by reference. Other accelerators are well known to those skilled in the art.

As examples of heat stabilizers for cured cyanoacrylate polymer there are the various compounds described in U.S. Pat. No. 5,306,752 (substituted quinoid compounds); U.S. Pat. No. 5,288,794 (aromatic compounds substituted with strong electron withdrawing groups and at least one leaving group); U.S. Pat. No. 5,328,944 (certain sulfur-containing compounds); and U.S. Pat. No. 5,424,343 (naphthosultones substituted with strong electron withdrawing groups), all of which are incorporated herein by reference.

In accordance with the present invention the adhesive is activated by contact with a multi-amine compound which includes at least three secondary or tertiary amine groups, at least one of the amine groups being a tertiary amine group. The multi-amine compound also has at least three terminal and/or pendant aliphatic hydrocarbon groups of at least four carbon atoms in length. Preferred multi-amine compounds include at least four secondary or tertiary amine groups, at least two tertiary amine groups, and have at least four terminal and/or pendant alkyl or alkenyl groups. Particularly suitable multi-amine compounds for use in the invention are based on multi-amine cascade compounds having the requisite number of amine groups as specified above and terminated with $C_4$ or higher alkyl or alkenyl groups.

Contact between the adhesive and the multi-amine compound may be accomplished by mixing immediately prior to bonding. Ordinarily, however, using the multi-amine compound in a primer composition will provide the most practical and convenient application to the substrate and will give effective bonding improvement on polyolefin substrates.

Without being bound thereby (it is believed that the terminal and/or pendant hydrocarbon groups of the multi-amine compounds utilized in the invention penetrate the polyolefin surface and become tangled in the polyolefin matrix, while the tertiary amine group(s) on the molecule activate polymerization of the anionically polymerizable adhesive.)

The terminal and/or pendant aliphatic hydrocarbon groups may be alkyl or alkenyl hydrocarbon groups. Linear or branched hydrocarbon groups may be used. Alkyl groups are preferred. Non-conjugated unsaturated long chain alkenyl groups, such as are found in some fatty acids and fatty alcohols may also be effectively employable as terminal and/or pendant hydrocarbon groups, but such groups might increase the susceptibility of the dendrimer to oxidation on storage. The length of the terminal and/or pendant alkyl or alkenyl groups is $C_4$ or higher, suitably $C_4$–$C_{22}$, preferably $C_8$–$C_{18}$, more preferably $C_{10}$–$C_{14}$, and especially preferably about $C_{12}$.

The multi-amine compound may be a multi-amine cascade compound having secondary or tertiary amine groups which are linked to at least one alkyl or alkenyl group of at least 4 carbon atoms. Preferred multi-amine cascade compounds used in the present invention have a structural formula characterized by a core unit; a plurality of branch units propagating generationwise from the core unit for a number of generations, n, each said branch unit including at least one secondary or tertiary amine nitrogen atom therein, and the number of generations being at least one, the number of branch units in each generation increasing by an integer factor of at least 2; and at three terminal group units terminating each branch unit of the nth generation, each said terminal group unit including a terminal $C_4$ or higher alkyl or alkenyl group.

Compounds with terminal or pendant primary amine groups, such as those prepared in accordance with *Synthesis*, 1978, pp 155–158 or U.S. Pat. No. 5,610,268, may be provided with terminal and/or pendant $C_4$ or higher alkyl groups by condensation of the starting amine terminated multi-amine with an appropriate $C_4$ or higher aldehyde, followed by reduction of the intermediate imine with a suitable reducing agent:

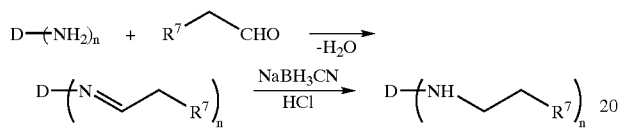

where D is the residue of the starting multi-amine compound and $R^7$ is a $C_4$ or higher alkyl group.

An example of this reaction is the condensation of a randomly branched poly(alkyleneimine) with an aldehyde followed by reduction of the resulting amine. For instance hyperbranched poly(ethylenimine) polymers represented by the simplified formula (1) shown below are commercially available from Aldrich Chemical Company, and from other sources, in number average molecular weight ranges varying from about 500 to about 100,000, and typically having primary, secondary and tertiary amines in the approximate ratio of 1:2:1. Such polymeric multi-amines may be reacted with dodecyl aldehyde followed by reduction of the intermediate imine with sodium cyanoborohydride. The product is a polymeric multi-amine terminated with dodecylamine groups at the branch ends to the main chain multi-amine (2). In addition this polymer may be converted to an all tertiary functionalized multi-amine by alkylation. For example, treatment of multi-amine (2) with n-butyl bromide provides the multi-amine (3) in which all the amine groups are tertiary. Polymers 12 and 13 and various intermediate polymers, may be used in the present invention.

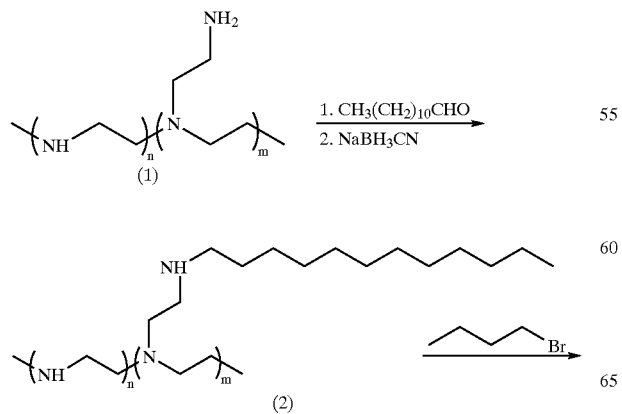

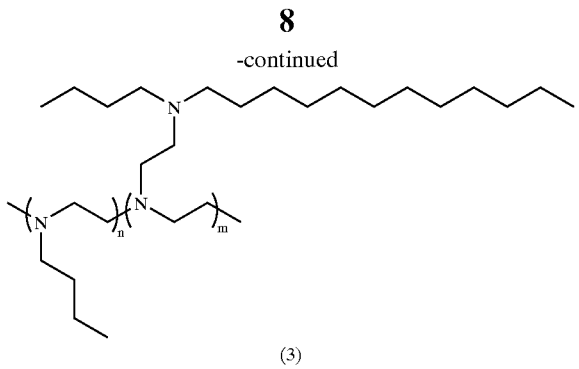

Similarly, multi-amines which are linear or branched addition polymers or copolymers of ethylenically unsaturated amines such as vinylamine, allylamine, aminopropyl vinyl ether and polymers derived from the condensation polymerization of diamines and diols may be converted to the corresponding alkylated polymers, which are also useful as primer materials for cyanoacrylate adhesives.

The condensation of primary amine end groups with alkyl aldehydes represents only one method for the attachment of aliphatic hydrocarbon groups to the multi-amine. Other procedures may also be used to give useful primer compounds. Such methods include reaction of an amino end group functionalized multi-amine with alkyl halides (RX), acid halides (RCOX) or alkyl acrylates ($CH_2$=CHCOOR), where X is halogen and R is alkyl, to give polymers with alkyl amine, alkyl amide or alkyl ester end groups:

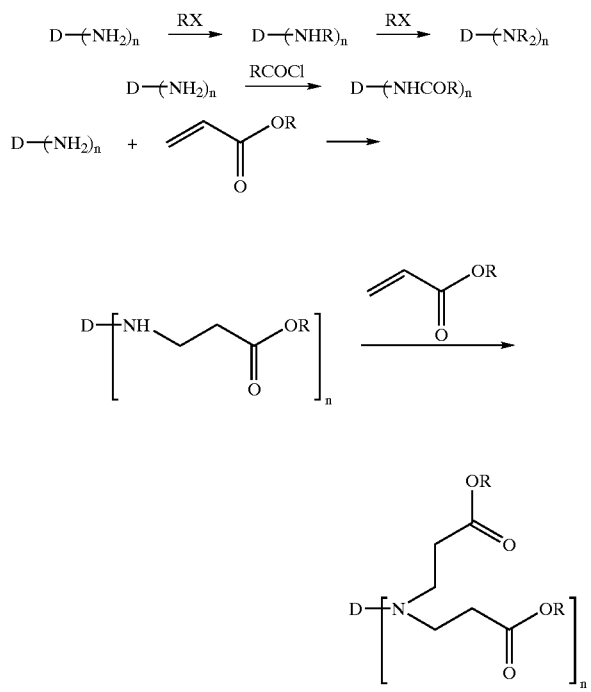

where D is the residue of the starting multi-amine.

One example of the alkyl halide reaction is given below:

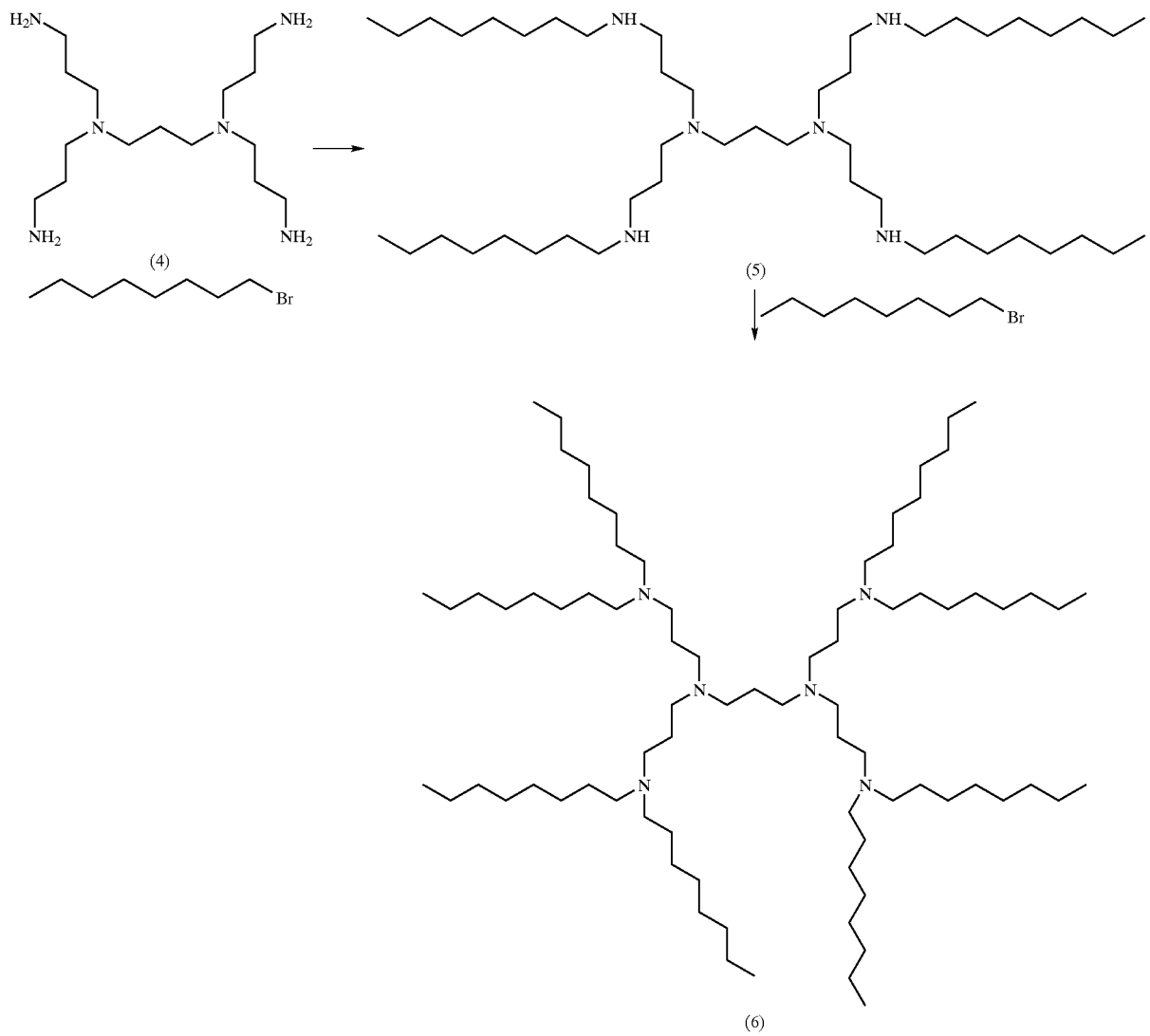

In this example, 1 mole of the starting amine (4) and 4 moles of octyl bromide are reacted to give tetra-octyl terminated multi-amine compound (5) having the alkyl groups directly linked to the multi-amine residues through secondary amino groups. This method, however, also allows the addition of a second alkyl group to be made on the secondary amine nitrogen atom. Thus the subsequent reaction of the product (5) with an additional 4 moles of octyl bromide gives the octaoctyl terminated multi-amine (6) having a bifurcated alkyl end structure as depicted above. Both the tetraoctyl and the octaoctyl products (5, 6), as well as intermediates therebetween, may be used in the present invention.

Another example of the alkyl halide reaction is given below:

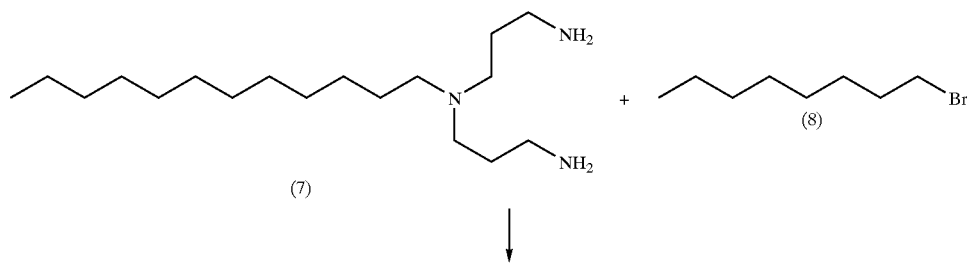

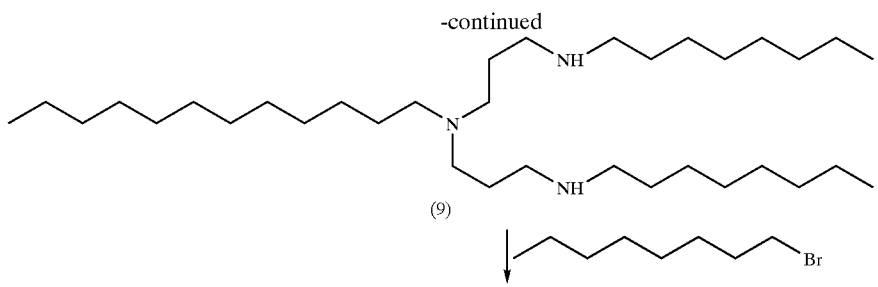

(9)

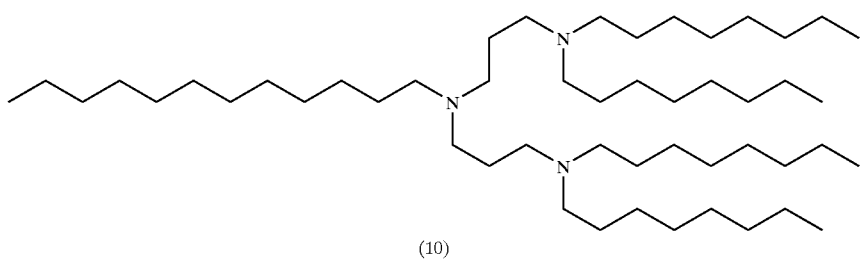

(10)

The starting amine (7) is prepared from dodecyl amnine and acrylonitrile according to the procedure described by Vögtle and coworkers in *Synthesis* 1978, pp 155–158. In this example, 1 mole of bis-(3-amninopropyl)dodecylamine (7) and 2 moles of octyl bromide (8) are reacted to give bis-(3-octylaminopropyl)dodecylamine (9). This product contains two secondary amine groups through which an additional two moles of octyl bromide may be added to give the tertiary branched amine tetra-octyl structure (10). Both the di-octyl and tetra-octyl products (9, 10), as well as intermediates therebetween, may be used in the present invention.

This procedure is also effective for the preparation of primers containing a higher degree of branching. For example, by means of the iterative synthetic process described in the above report by Vögtle, the multi-amine (7) may be converted to the multi-amine (11), containing four primary amine groups to which up to eight alkyl groups may be attached. When hexyl bromide (12) is used as the alkylating agent, the cascade type multi-amines (13) and (14) are obtained following the addition of four and eight moles of halide respectively:

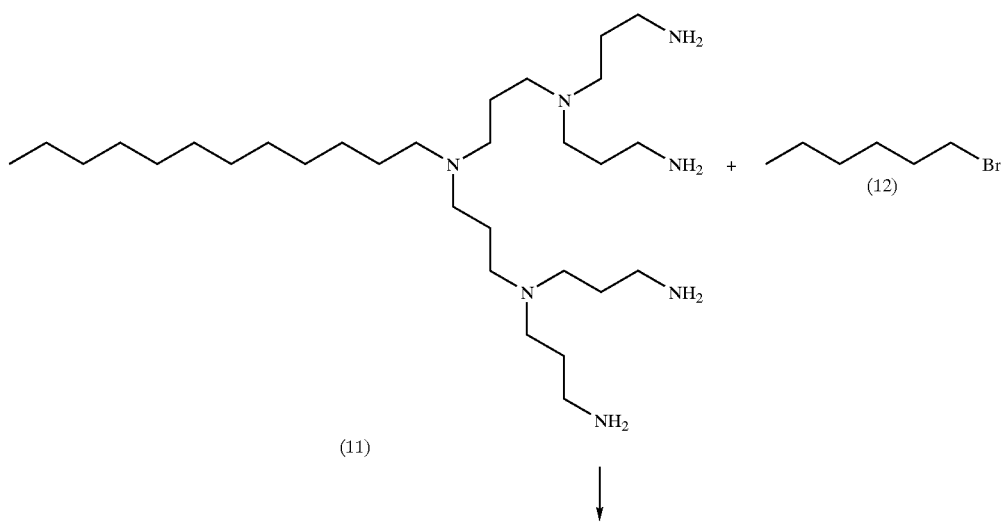

-continued

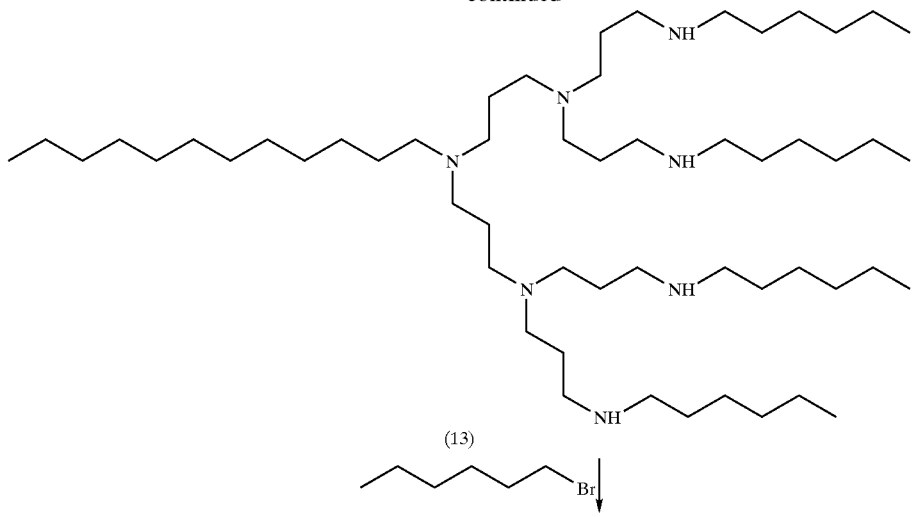
(13)

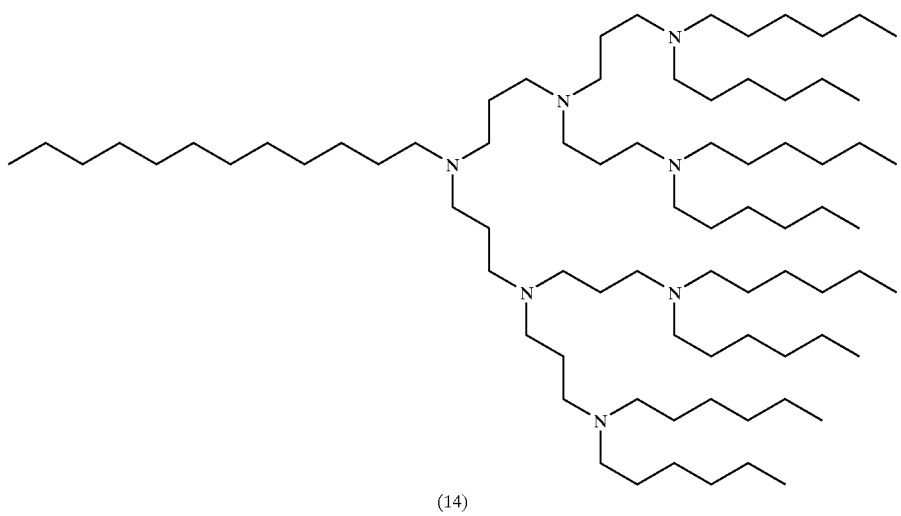
(14)

Useful multi-amines may also be obtained by the alkylation of linear and branched polyalkyleneamines. For example, the alkylation of linear poly(ethylenimine) (15) with dodecylbromide provides a comb-like multi-amine (16) containing dodecyl groups pendent to the main chain multi-amine. This polymer may be used in the practice of the current invention. The number of repeat units in the polymer is indicated by n and this may vary over a wide range.

Alkyl group attachment to a multi-amine may also be accomplished by the reaction of the multi-amine with a suitable $C_4$–$C_{22}$ alkyl acrylate or methacrylate by means of a Michael addition reaction. For example, the reaction of the previously described branched polyethylenimine (1) and 2-ethylhexyl acrylate (17) gives the corresponding dodecyl functionalized multi-amines (18, 19) following the addition of primary and secondary amine groups respectively.

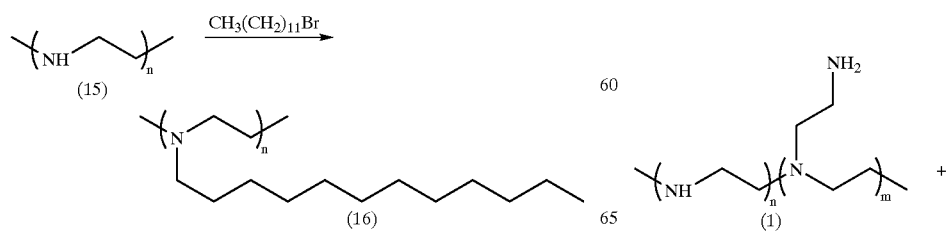

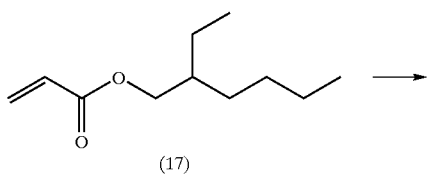

(17)

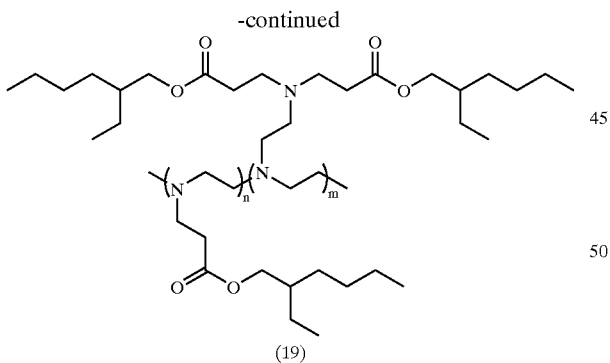

(18)

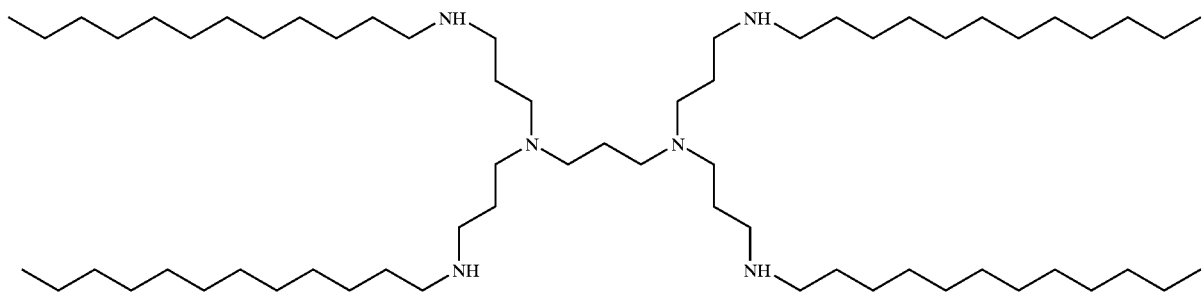

(19)

As an example of the acid halide reaction, one mole of the primary amine terminated multi-amine (11), shown above may be reacted with 4 moles of stearoyl chloride to give the corresponding multi-amine having four terminal stearyl amide groups thereon.

Hydroxyl terminated multi-amine dendrimers, such as those described in Coleshill, A., et al, *Polymer Preprints*, 38(1) 135 (4/1997), may be provided with $C_4$ or higher terminal aliphatic hydrocarbon group by esterification with a suitable carboxylic acid, or carboxylic acid chloride such as stearoyl chloride, or by etherification with a $C_4$ or higher alcohol, for instance 1-butanol, 1-octanol, or a fatty alcohol.

It is also possible to prepare useful multi-amine primers with mixed alkyl groups and in certain cases partially alkylated materials may be useful, although it is expected that adhesive performance will be optimal for the fully alkylated derivatives.

Other techniques for providing branched multi-amine compounds with $C_4$ or higher aliphatic hydrocarbon groups as end groups will be readily apparent to the skilled organic synthetic chemist and the resulting structures are intended to be covered by the disclosure and claims hereof.

One class of alkyl terminated multi-amine compounds useful in the practice of the present invention are cascade compounds based on a core residue from a diamine molecule $H_2N$—$R^8$—$NH_2$ where $R^8$ is a divalent hydrocarbon group, which may be aliphatic or aromatic and is suitably $C_2$–$C_6$ alkylene. Specific examples of such cascade compounds include the following:

D1—dodecylamine terminated poly(propyleneamine) dendrimer on 1,3-diaminopropane core—generation 1 (G1):

D2—dodecylamine terminated poly(propyleneamine) dendrimer on 1,3-diaminopropane core—generation 2 (G2):

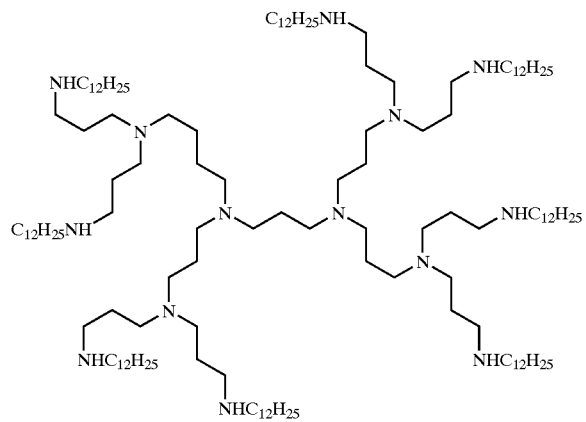

D3—dodecylamine terminated poly(propyleneamine) dendrimer on 1,3-diaminopropane core—generation 3 (G3):

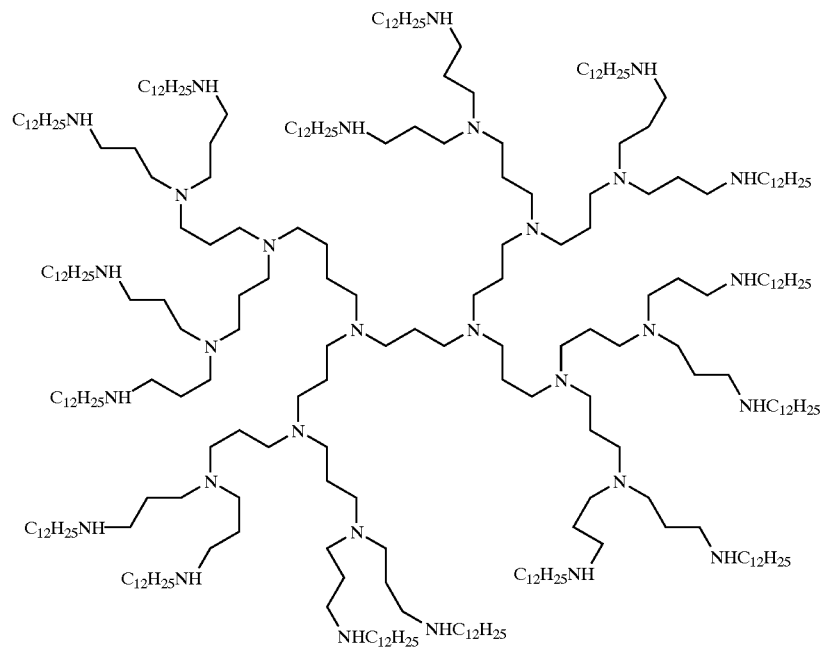
D4—dodecylamine terminated poly(propyleneamine) dendrimer on 1,4-diaminobutane core—generation 4 (G4):
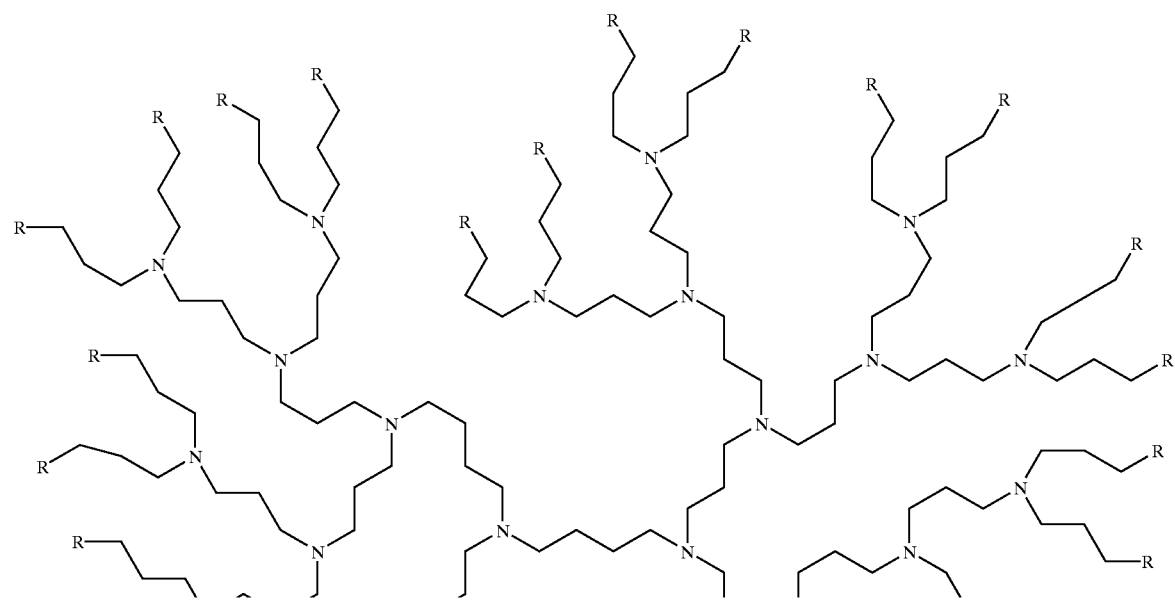

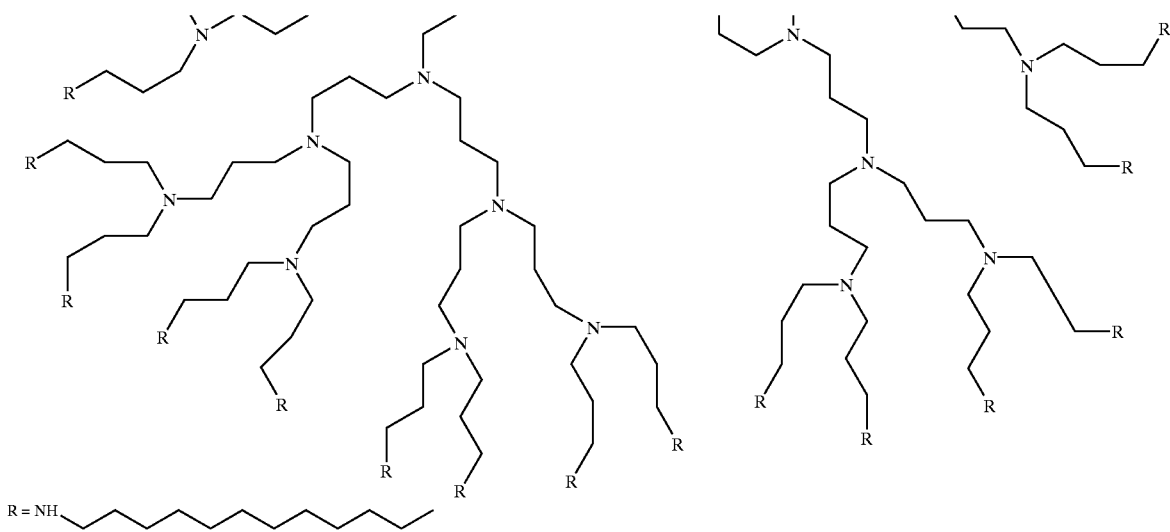
R = NH—(long alkyl chain)
D5 dodecylamine terminated poly(propyleneamine) dendrimer on 1,4-diaminobutane core—generation 5 (G5):
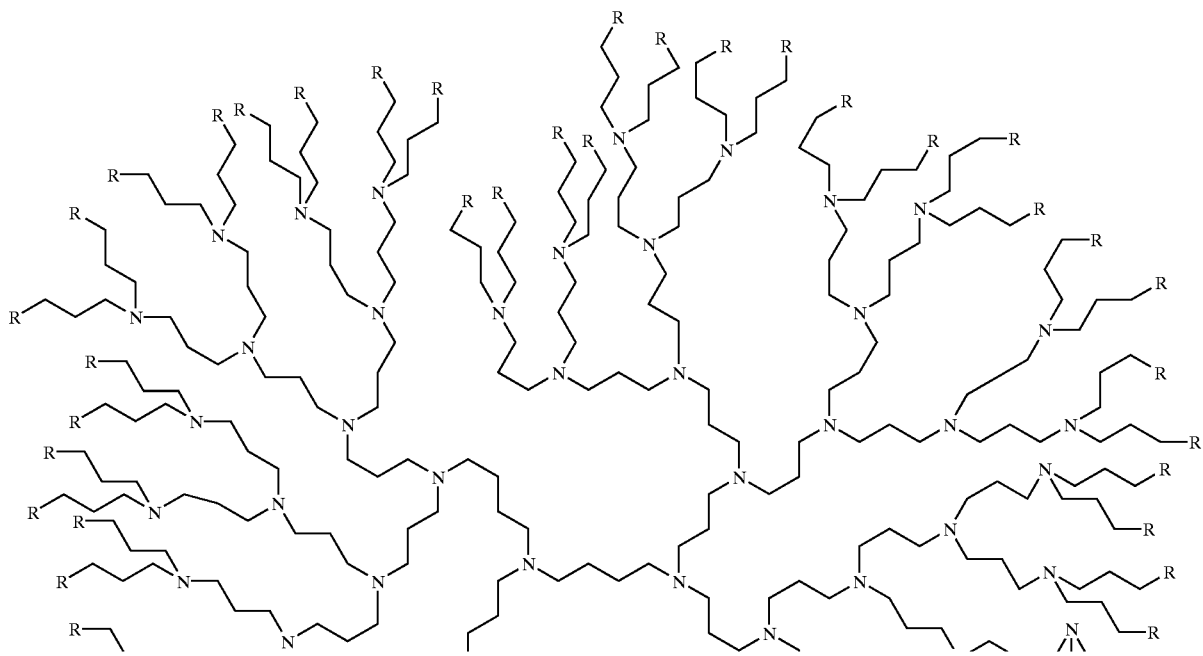

-continued

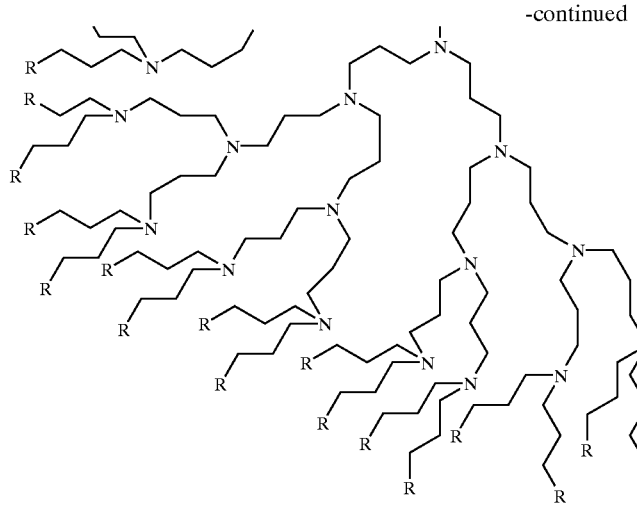
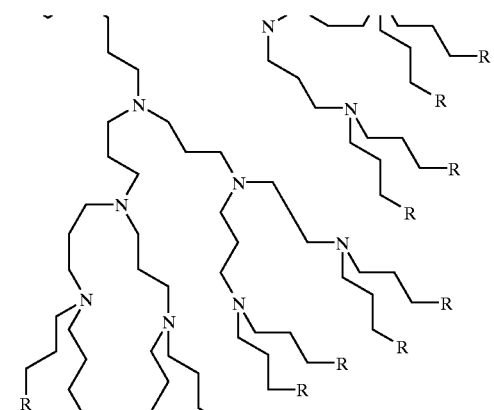

where R is the same as for D4. Other suitable structures are provided in Examples 1 and 2 below.

Still other suitable cascade compounds are based on core moieties which are primary mono-amines, such as described by Vögtle and coworkers in *Synthesis*, 1978, pp 155–158. Secondary amines may also be employed as core moieties for such multi-amine cascade compounds.

In other variations on the invention, carboxylate end-functionalized multi-amine cascade compounds as disclosed in U.S. Pat. Nos. 4,507,466 and 5,527,524, incorporated herein by reference, and commercially available under the tradename Starburst™ Dendrimer, may be alkylated by known esterification procedures to give useful primer products.

In some cases the hydrocarbon terminated multi-amine compound may be applied neat but usually will be most conveniently applied from a solution in a volatile solvent. Suitable solvents include alcohols, heptane, trichloroethane, acetone and mixtures thereof. The multi-amine compound is preferably used at a concentration of from about 0.01% to about 2% by weight in the solvent, more preferably from about 0.1% to about 1.0% by weight. After application of the primer solution the solvent is allowed to dry and then the anionically polymerizable monomer adhesive composition is applied (preferably within about 30 minutes after the solvent has been evaporated) and the substrates are promptly joined and held until the adhesive fixtures. If both substrates are low surface energy materials such as polyolefins, the primer is desirably applied to both. If only one is a low energy substrate, the primer may be applied to only that substrate.

The invention is illustrated by the following non-limiting examples.

EXAMPLES

Example 1

This example illustrates the condensation reaction of a primary amine terminated multi-amine with an alkyl aldehyde followed by reduction of the resulting imine to give an alkyl terminated multi-amine of the invention.

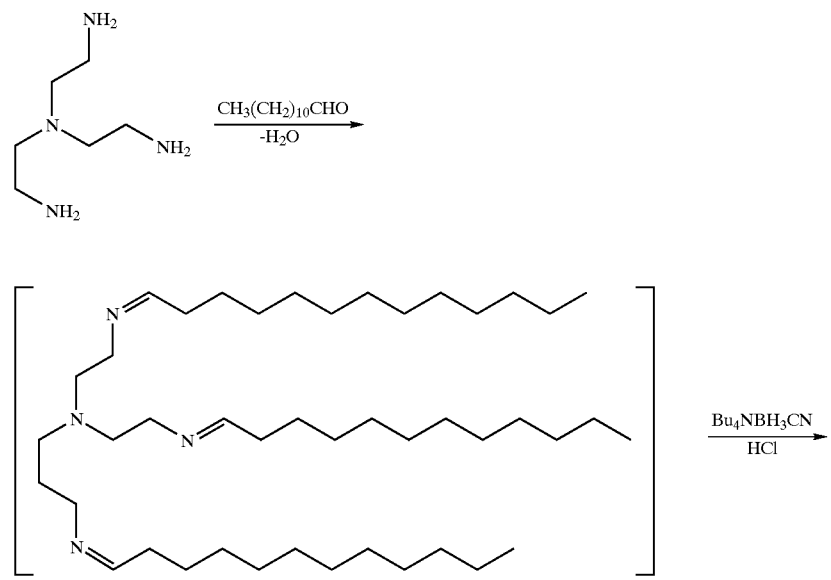

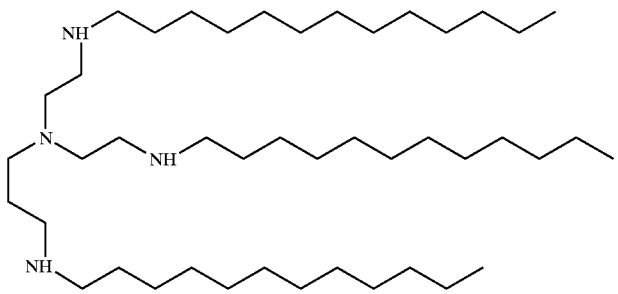

To a 500 ml, 3-necked reaction flask equipped with a dropping funnel, thermocouple, nitrogen head purge, magnetic stirrer and cooling bath was added tris-(2-aminoethyl) amine (TAA) (2.011 g, 0.014 moles), powdered activated molecular sieves (8.021 g, 4 Angstroms) and dichloromethane (155 ml). The mixture was cooled to 4° C. and dodecyl aldehyde (8.649 g; 0.047 moles) was added dropwise over 10 minutes to the stirred mixture. The temperature of the reaction mixture increased to 80° C. during the addition of the aldehyde. Stirring and cooling were continued for 4 hours and tetrabutylammonium cyanoborohydride (8.178 g; 0.029 moles), additional dichloromethane (10 ml) and a solution of hydrogen chloride in diethyl ether (84 mls; 1.0 M) were added sequentially to the reaction mixture. The ice-bath was removed and the mixture stirred for a further 24 hours at room temperature.

The solvent was removed under reduced pressure and hydrochloric acid (200 ml; 0.5 M) was added to the residue, which was then extracted with dichloromethane (3×100 ml).

The combined organic extracts were washed with saturated sodium bicarbonate solution (2×100 ml) and filtered. The filtrate was concentrated to about 50 ml under reduced pressure, washed with water (3×50 ml) and dried over sodium sulfate. The dried solution was filtered and the solvent removed to yield a yellow colored, wax-like product (identified from spectral analysis as tris-(2-dodecylaminoethyl)amine (TDAA))6.766 g; 74% yield). $^1$H NMR (CDCl$_3$): δ 0.9, m, 9 H, methyl group protons; δ=1.3, s, 60 H, methylene group protons; δ=2.1, broad s, 3H, N$\underline{H}$ secondary amine protons; δ=2.6, m, 12 H, NC$\underline{H_2}$C$\underline{H_2}$NH; δ=2.7, m, 6H, —CH$_2$CH$_2$C$\underline{H_2}$NH. IR (KBr film): 3295 cm$^{-1}$ NH stretching vibration of secondary amine groups; 2930 cm$^{-1}$, CH stretching vibration of methylene groups.

Example 2

The specific cascade compounds identified as D1–D5, above, were obtained by the reaction of the corresponding primary amine terminated multi-amine starting compound (obtained in the manner of Meijer, U.S. Pat. No. 5,610,268) and dodecyl aldehyde according to the procedure of Example 1. All were soluble in heptane (D3 gave slightly cloudy solution).

Example 3

The alkyl terminated multi-amine products of Examples 1 and 2 were used as primers (at 0.5% concentration in heptane) for bonding polyolefins with cyanoacrylate adhesives, and the bonded assemblies were tested by measuring the lap shear strengths. Three different polyolefin test substrates were used: low density polyethylene (LDPE), high density polyethylene (HDPE) and polypropylene (PP). The dimensions of the substrates were 25.4 mm×25.4 mm×6.0 mm. Two commercial primer solutions, one containing DBU (Primer 770, Loctite Corp.), and the other containing TDA (Primer 793, Loctite Corp.), were included for comparative purposes, as was an unprimed sample.

The substrate edges were deburred, where necessary, wiped with isopropanol and allowed to dry. The test substrates were arranged in pairs and primed by brushing one side of each test piece with the appropriate primer solution. The primed substrates were allowed to stand at room temperature for 15 minutes to ensure complete evaporation of the solvent and to ensure that the new primers have a sufficiently long on-part activity to warrant commercial consideration. Two drops of Loctite Adhesive Product 414 (ethyl cyanoacrylate-based adhesive formulation) were applied to the ends of one of the primed surfaces of each pair and an adhesive joint assembled by pressing the second primed substrate to the adhesive drops on the first piece, such that a 25.4×12.7 mm$^2$ overlap joint was obtained. Finger pressure was maintained for 30 seconds immediately after assembly and the assembled joint was allowed to stand at room temperature for at least 48 hours before testing.

Adhesive strength measurements were determined according to ASTM D4501: *Shear Strength of Adhesive Bonds Between Rigid Substrates by the Block-shear Method*, at a constant strain rate of 12.7 mm/min. The stress at maximum load ($\sigma_{max}$) and mode of failure were recorded. Five test specimens were prepared for each primer/substrate combination. The results obtained are summarized in the following Table 1 where stress values are average of 5 measurements and the coefficient of variation refers to the standard deviation expressed as a percentage of the mean.

TABLE 1

Block-shear adhesive strength evaluation of ethyl CA/dendrimer primers (D1–D5)

| | LDPE | | | HDPE | | | PP | | |
|---|---|---|---|---|---|---|---|---|---|
| Primer | $\sigma_{max}$ (MPa) | coeff. var. (%) | fail mode | $\sigma_{max}$ (MPa) | coeff. var. (%) | fail mode | $\sigma_{max}$ (MPa) | coeff. var. (%) | fail mode |
| Comparative | | | | | | | | | |
| None | 0 | — | — | 0 | — | — | 0.5 | 18 | A/C |
| DBU | 0.4 | 23 | A/C | 0.6 | 17 | A/C | 1.4 | 40 | A/C |
| TDA | 1.2 | 45 | A/C | 8.6 | 29 | A/C | 13.3 | 19 | S |
| Invention | | | | | | | | | |
| TDAA | 3.2 | 43 | A/C | — | — | — | — | — | — |
| D1 | 6.9 | 5 | S | 14.5 | 14 | S | 18.9 | 13 | S |
| D2 | 6.5 | 10 | S | 11.6 | 30 | S | 13.9 | 30 | S |
| D3 | 6.8 | 14 | S | 7.2 | 74 | A/C | 17.5 | 20 | S |
| D4 | 6.0 | 16 | S | 11.9 | 38 | A/C | 18.7 | 11 | S |
| D5 | 6.1 | 16 | S | 12.7 | 32 | A/C | 22.3 | 7 | S |

($\sigma_{max}$ = stress at maximum load;
S = substrate failure;
A/C = adhesive and/or cohesive failure)

The mode of failure has important consequences for adhesive performance. Substrate failure (S) indicates that the adhesive bond strength exceeds the bulk shear strength of the polyolefin test substrate. In the above experiments, substrate failure was associated with extensive plastic deformation and fibrillation of the substrate surface and indicates that an interpenetration of the primer/adhesive system with the substrate surface has occurred at a molecular level. Such a mechanism is considered important in providing an adhesive joint with good environmental durability. In contrast, adhesive failure at the adhesive/substrate interface or cohesive failure within the cyanoacrylate adhesive (A/C), resulted in a much smoother fracture surface, indicating that little or no primer had penetrated into the substrate surface during or after the bonding process.

From the data in Table 1 it can be seen that the adhesive strength on all substrates without primer is either very low or non-existent. This result is generally what is expected from previous reports and highlights the necessity of using a primer for bonding polyolefins with cyanoacrylates.

The following observations are also taken from the data in Table 1.

LDPE:

(Multi-amine TDAA showed significant improvement in bond strength over the prior art primers based on DBU and TDA.) However, even more striking results were obtained with the primers containing products D1–D5 on LDPE. With these latter primers, the adhesive joints all consistently failed in the substrate. This compares very favorably to the performance of the commercial primer compositions, which failed at low adhesive strengths and in A/C mode. For the series D1–D5 the performance on LDPE was, independent of the generation number of the cascade compound. Because of their excellent performance on LDPE, additional data for compounds D1–D5 was also collected for HDPE and PP substrates.

HDPE:

D1 and D2 showed good performance on HDPE, with substrate failure recorded in both cases. D4 and D5, which fail in adhesive/cohesive mode, have significantly higher bond strength than either of the commercial primers. D3 gave a relatively lower strength than the other dendrimers, but the very large coefficient of variation associated with this data set suggests poor experimental control and therefore, it may be disregarded in an overall assessment of the cascade compound performance. Close inspection of the D3 substrates showed no obvious cause for the variability but the failure mode was clearly adhesive/cohesive with little or no substrate damage. In general therefore, the new materials exceed the performance of the commercial primers on HDPE, although there is a change in the mode of failure, from substrate to adhesive/cohesive, as the generation number of the polymer increases.

PP:

Each of the cascade compounds D1–D5 gave good performance on PP, with substrate failure being observed in every case. In this regard, the performance is comparable to that of the existing primer product based on TDA and exceeds that of the primer product based on DBU. Additionally, the bond strengths at failure were comparable or better in all cases to the TDA product. Still further, the degree of blooming (an undesirable formation of white polycyanoacrylate film on the non-bonded portion of the substrate, close to the adhesive fillet and caused by monomer evaporation from the fillet/bondline during exothermic polymerization) was significantly less for the dendrimer samples, than for the existing primer products.

Example 4

Multi-amine cascade compounds may be prepared starting from tris-(2-aminoethyl)amine (TAA) and performing Michael addition followed by catalytic reduction of the intermediate nitrile according to the procedure of Meijer in U.S. Pat. No. 5,610,268. The sequence is readily carried out to at least generation 5 (based on TAA as the core moiety). Following the procedure of Example 1, condensation of the final generation primary amine with an appropriate $C_4$–$C_{22}$ aldehyde will yield alkyl terminated multi-amine dendrimers of the invention. The first and second generation products are depicted below:

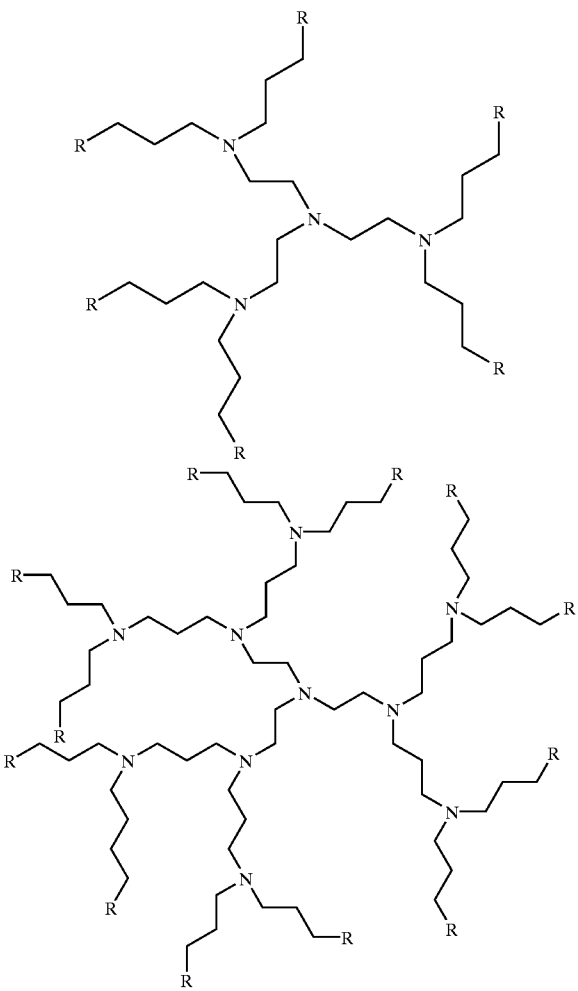

where R is NHR⁴ and R⁴ is as previously defined.

Those skilled in the art will understand that many other variations, not specifically discussed herein, may practiced in light of the teachings provided and such variations should be considered to come within the scope of the present invention.

We claim:

1. A primer composition for anionically polymerizable monomer adhesives, the primer composition comprising a multi-amine compound in a volatile organic solvent, the multi-amine compound having at least three amine groups which are secondary or tertiary amine groups, at least one of said amine groups being a tertiary amine group, and the multi-amine compound further having at least three terminal and/or pendant aliphatic hydrocarbon groups thereon which are higher than $C_4$.

2. A primer composition as in claim 1 wherein said multi-amine compound has at least four said amine groups and at least four said terminal and/or pendant aliphatic hydrocarbon groups, said aliphatic hydrocarbon groups being alkyl or alkenyl groups.

3. A primer composition as in claim 1 wherein said multi-amine compound is present in the composition at a concentration of from about 0.01% to about 2% by weight of the composition.

4. A primer composition as in claim 1 wherein said volatile organic solvent is a hydrocarbon solvent.

5. A primer composition as in claim 1 wherein said multi-amine compound has at least two tertiary amine groups thereon.

6. A method of bonding a pair of substrates comprising applying a primer composition as in claim 1 to at least one of said substrates, allowing the volatile organic solvent to evaporate, subsequently applying an α-cyanoacrylate monomer formulation to at least one of said substrates, and then joining the substrates until the adhesive fixtures.

7. A method as in claim 6 wherein the multi-amine compound in said primer composition is a multi-amine cascade compound terminated with $C_8$–$C_{18}$ alkyl groups and at least one of the substrates is low density polyethylene.

8. A primer composition for anionically polymerizable monomer adhesives, the primer composition comprising a multi-amine compound in a volatile organic solvent, the multi-amine compound having at least three amine groups which are secondary or tertiarn amine groups, at least one of said amine groups being a tertiary amine group, the multi-amine compound further having at least three terminal and/or pendant $C_4$ or higher aliphatic hydrocarbon groups thereon, and wherein said multi-amine compound is a linear or branched poly(alkyleneamine) polymer, a multi-amine cascade compound or an addition polymer or copolymer of an ethylenically unsaturated amine.

9. A primer composition as in claim 8 wherein said multi-amine compound is a multi-amine cascade compound and the terminal and/or pendant aliphatic hydrocarbon groups are $C_4$–$C_{22}$ alkyl or alkenyl groups.

10. A primer composition as in claim 8 wherein said terminal and/or pendant aliphatic hydrocarbon groups are $C_8$–$C_{18}$ alkyl groups.

11. A method of bonding a pair of substrates comprising applying a primer composition as in claim 8 to at least one of said substrates, allowing the volatile organic solvent to evaporate, subsequently applying an α-cyanoacrylate monomer formulation to at least one of said substrates, and then joining the substrates until the adhesive fixtures.

12. An adhesive composition obtained by bringing a multi-amine compound into contact with a formulation comprising an anionically polymerizable monomer of the formula:

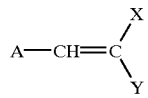

where X and Y are groups which are more strongly electron withdrawing than halo and A is H or $CH_2=CH-$, the multi-amine compound having at least three amine groups which are secondary or tertiary amine groups, at least one of said amine groups being a tertiary amine group, and the multi-amine compound further having at least three terminal and/or pendant aliphatic hydrocarbon groups thereon which are higher than $C_4$.

13. An adhesive composition as in claim 12 wherein the anionically polymerizable monomer is an α-cyanoacrylate ester monomer, the multi-amine compound has at least four amine groups and at least four said terminal and/or pendant aliphatic hydrocarbon groups thereon, and the terminal and/or pendant aliphatic hydrocarbon groups are alkyl or alkenyl groups.

14. A bonded assembly comprising a pair of substrates adhesively joined by a cured cyanoacrylate adhesive as in claim 13.

15. A bonded assembly as in claim 14 wherein at least one of said substrates is a polyolefin.

16. A bonded assembly as in claim 15 wherein said polyolefin is selected from the group consisting of high density polyethylene, low density polyethylene and polypropylene.

17. A bonded assembly as in claim 15 wherein said α-cyanoacrylate ester monomer has been brought into contact with said multi-amine compound by application of the monomer to a surface of said polyolefin substrate which has been primed with said multi-amine compound.

18. A cyanoacrylate adhesive composition as in claim 13 wherein said terminal and/or pendant alkyl or alkenyl groups are $C_8$–$C_{18}$ alkyl groups.

19. A cyanoacrylate adhesive composition as in claim 13 wherein the terminal and/or pendant alkyl or alkenyl groups are $C_{10}$–$C_{14}$ alkyl groups.

20. A cyanoacrylate adhesive composition as in claim 13 wherein the multi-amine compound is a cascade compound having a structural formula which includes a core unit; a plurality of branch units propagating generationwise for a number of generations, n, from the core unit, each said branch unit including therein at least one secondary or tertiary amino group therein, and the number of generations being at least one, the number of branch units in each generation increasing by an integer factor of at least 2; and, a plurality of terminal group units terminating each branch unit of the nth generation, the terminal group units comprising said terminal and/or pendant $C_4$ or higher alkyl or alkenyl groups.

21. An adhesive composition as in claim 12 wherein said multiamine compound has been brought into contact with said anionically polymerizable monomer by application of the monomer to a surface which has been primed with said multiamine compound.

22. An adhesive composition as in claim 12 wherein said multi-amine compound has been brought into contact with said anionically polymerizable ester monomer by mixing the anionically polymerizable monomer and the multi-amine compound.

23. An adhesive composition as in claim 12 wherein said terminal and/or pendant aliphatic hydrocarbon groups are $C_8$ or higher.

24. A cyanoacrylate adhesive composition obtained by bringing a multi-amine compound into contact with a formulation comprising an α-cyanoacrylate ester monomer, the multi-amine compound having at least three amine groups which are secondary or tertiary amine groups, at least one of said amine groups being a tertiary amine group, the multi-amine compound further having at least three terminal and/or pendant $C_4$ or higher aliphatic hydrocarbon groups thereon, and wherein the multi-amine compound is a linear or branched poly(alkyleneamine) polymer, a multi-amine cascade compound or an addition polymer or copolymer of an ethylenically unsaturated amine.

25. A cyanoacrylate adhesive composition as in claim 24 wherein the multi-amine compound is a multi-amine cascade compound terminated with $C_4$–$C_{22}$ alkyl or alkenyl groups.

26. A cyanoacrylate adhesive composition as in claim 25 wherein the multi-amine cascade compound is a poly (alkyleneamine).

27. A cyanoacrylate adhesive composition as in claim 26 wherein the poly(alkyleneamine) cascade compound has a generation number of 1–5.

28. A cyanoacrylate adhesive composition as in claim 26 wherein the alkylene groups of said poly(alkyleneamine) cascade compound are $C_2$–$C_4$ alkylene groups.

29. A cured cyanoacrylate polymer obtained by bringing a multi-amine compound into contact with a composition comprising an α-cyanoacrylate ester monomer, the multi-amine compound being selected from the group consisting of linear or branched poly(alkyleneamine) polymers, multi-amine cascade compounds and addition polymers or copolymers of ethylenically unsaturated amines, and having at least three terminal and/or pendant $C_4$ or higher alkyl groups.

30. A cured cyanoacrylate polymer as in claim 29 wherein the multi-amine compound is a poly(alkyleneamine) cascade compound.

31. A cured cyanoacrylate polymer as in claim 30 wherein the terminal and/or pendant alkyl groups of said multi-amine compound are $C_8$–$C_{18}$ alkyl groups.

32. A cured cyanoacrylate polymer as in claim 30 wherein the alkylene groups of said poly(alkyleneamine) cascade compound are $C_2$–$C_4$ alkylene groups.

33. A primer composition for anionically polymerizable monomer adhesives, the primer composition comprising a multi-amine compound of the formula:

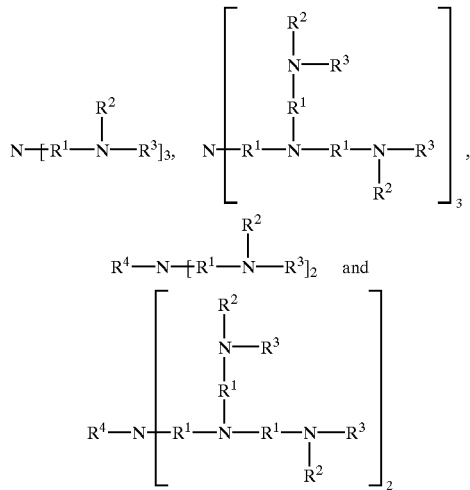

where $R^1$ is —$CH_2CH_2$— or —$CH_2CH_2CH_2$—; $R^2$ is H or $R^3$; the $R^3$ groups are the same or different $C_4$–$C_{22}$ alkyl, $C_4$–$C_{22}$ alkenyl, carboxy-$C_4$–$C_{22}$-alkyl, carboxy-$C_4$–$C_{22}$-alkenyl or —$CH_2CH_2C(=O)OR^4$ groups; and $R^4$ is $C_4$–$C_{22}$ alkyl, and, linear or branched poly(alkylenimine) having at least three terminal and/or pendent groups defined as for $R^3$.

34. A primer composition as in claim 33 wherein $R^3$ is $C_8$–$C_{18}$ alkyl or carboxyalkyl.

35. A primer composition as in claim 34 wherein $R^2$ is H and $R^3$ is dodecyl.

36. A method of bonding a pair of substrates comprising applying a primer composition to at least one of said substrates, allowing the volatile organic solvent to evaporate, subsequently applying an α-cyanoacrylate monomer formulation to at least one of said substrates, and then joining the substrates until the adhesive fixtures, wherein the primer composition comprises a multi-amine compound in a volatile organic solvent, the multi-amine compound having at least three amine groups which are tertiary or secondary amine groups, at least one of said amine groups being a tertiary amine group, and the multi-amine compound further having at least three terminal and/or pendant $C_4$ or higher aliphatic hydrocarbon groups thereon, and at least one of said substrates is a polyolefin.

* * * * *